United States Patent
Buttram

(10) Patent No.: US 6,769,957 B2
(45) Date of Patent: Aug. 3, 2004

(54) CREEPING WAVE TECHNIQUE FOR MILL ROLL INSPECTION

(75) Inventor: Jonathan D. Buttram, Bedford, VA (US)

(73) Assignee: Innerspec Technologies, Inc., Lynchburg, VA (US)

( * ) Notice: Subject to any disclaimer, the term of this patent is extended or adjusted under 35 U.S.C. 154(b) by 154 days.

(21) Appl. No.: 09/896,504

(22) Filed: Jun. 29, 2001

(65) Prior Publication Data

US 2003/0013388 A1 Jan. 16, 2003

(51) Int. Cl.[7] .............................................. B24B 49/00
(52) U.S. Cl. .............................. 451/5; 451/10; 451/11; 451/51; 451/910; 73/622; 73/644
(58) Field of Search ................... 451/5, 6, 9, 10, 451/11, 51, 910; 73/622, 644

(56) References Cited

U.S. PATENT DOCUMENTS

| | | | | |
|---|---|---|---|---|
| 3,255,626 A | * | 6/1966 | Van Der Veer | |
| 3,850,027 A | * | 11/1974 | Nakanishi et al. | 73/67.8 S |
| 4,472,975 A | * | 9/1984 | Beck et al. | 73/644 |
| 5,433,113 A | * | 7/1995 | Andoh et al. | 73/622 |

* cited by examiner

*Primary Examiner*—Eileen P. Morgan
(74) *Attorney, Agent, or Firm*—James W. Hiney

(57) ABSTRACT

A method and apparatus for simultaneously inspecting and grinding roll mills which utilizes a transducer assembly which produces a creeping wave propagation in conjunction with a couplant fluid provider and data acquisition circuit which allows the operator to see the crack and imperfections in on the surface of the mill rolls as they are rotated and to grind them off.

16 Claims, 4 Drawing Sheets

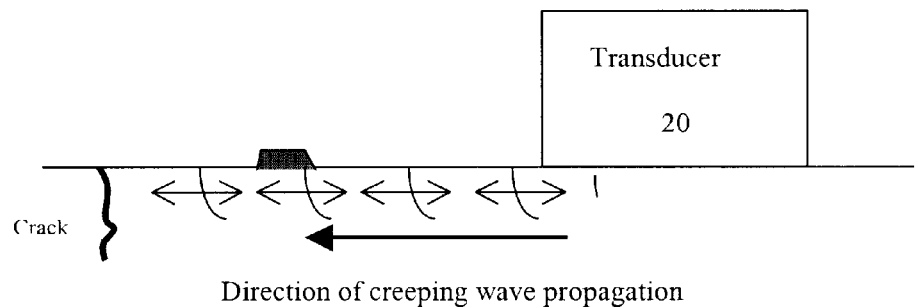
Figure 1: Creeping wave propagating underneath surface contaminates without effect.
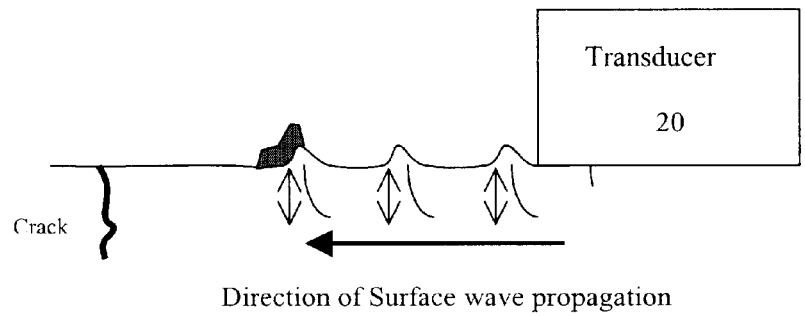
Figure 2: Surface wave is effected by surface contaminate.

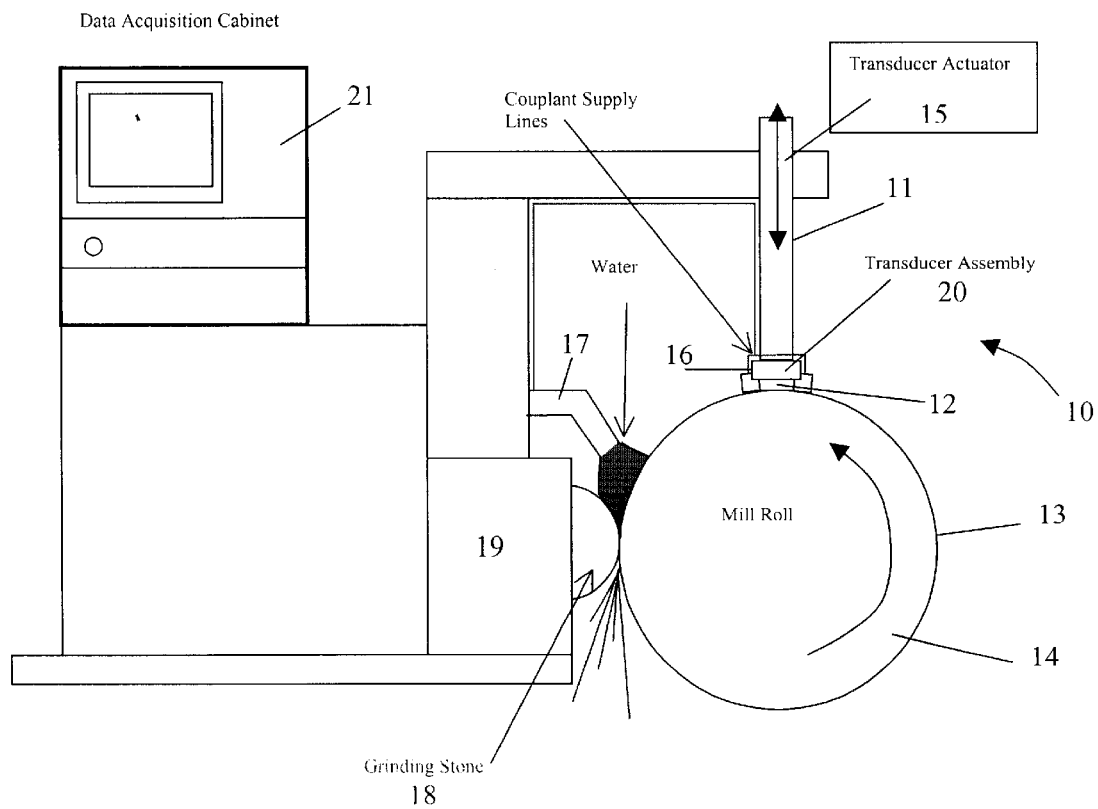
Figure 3: Roll grinding machine with creeping wave inspection system

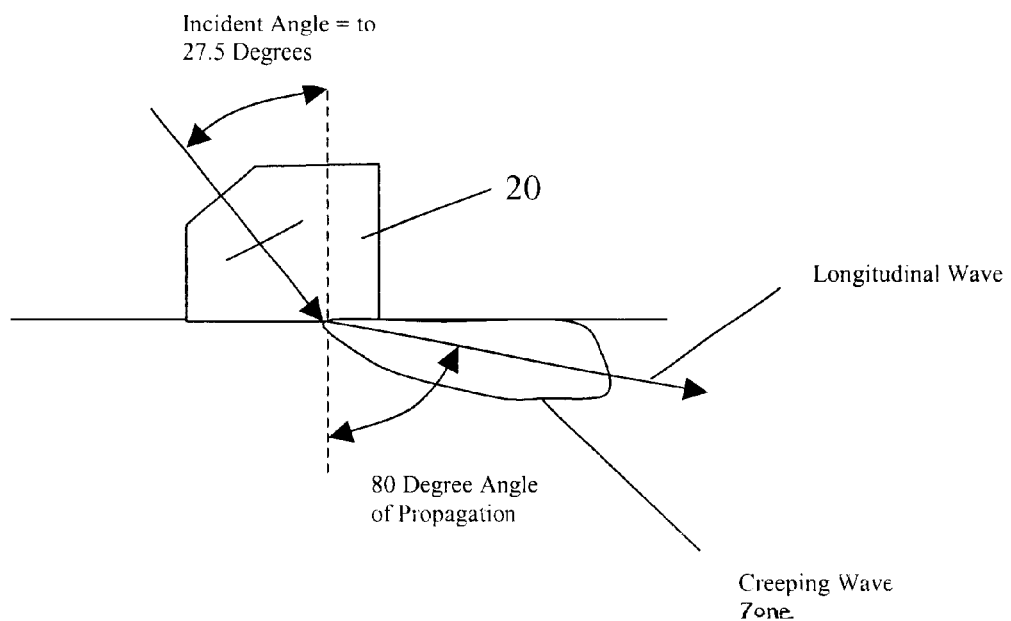
Figure 4: Creeping wave transducer

CREEPING WAVE TECHNIQUE FOR MILL ROLL INSPECTION

1.0 FIELD OF INVENTION

This invention relates, overall to an automated ultrasonic inspection system of mill rolls used in the process of metal fabrication, and, in particular to the use of creeping waves as the specific wave mode used for the detection of surface and near surface defects such as cracks, porosity, etc.

2.0 BACKGROUND

Mill rolls are an integral component of many metal fabricating processes. The rolling surface of a mill roll is typically subjected to high cyclic stresses created by direct loading and/or thermal cycles. The result is the formation of surface cracks that can quickly propagate to failure if not detected and removed. For this reason, mill rolls are periodically removed from service and placed in a roll grinding machine that mechanically removes a work hardened layer of material from the rolling surface. The rolls are then inspected to assure that all cracks are removed prior to reintroducing back into the mill.

The most common ultrasonic method for roll inspection is performed using a handheld Surface Wave (also called Raleigh Wave) ultrasonic transducer. This process involves applying couplant along the top of the roll and slowly moving the transducer down the roll axis while propagating sound in the circumferential direction. At the completion of this test, the roll is then turned 180 degrees and the procedure repeated. This manual exam was later developed into an automated technique where the transducer is mechanically held and scanned down the roll as the roll is rotated. However, automation of the Surface Wave technique for roll inspection never developed into a commercial success due to problems associated with water on the roll surface as described below. A serious complication to using Surface Waves for roll inspection is the sensitivity that this wave mode has to the presence of fluid, such as water drops, on the roll surface. A Surface Wave creates very small displacements in the direction perpendicular to the surface plane. As a result, any substance on the roll surface, such as a water drop, will be displaced as the wave front moves underneath it. This has two effects on the Surface Wave: 1) energy is removed from the wave front and 2) a reflected signal is produced that returns to the transducer from the water drop. The resulting reflected signal can appear identical to that produced by a surface breaking crack. Therefore, it is critical that all water, oil, etc, be removed from the roll surface prior to testing when using Surface Waves. This is made more difficult since cooling fluids are used during the grinding of the roll surface. In addition, conventional ultrasonic transducers require the use of fluid between the roll surface and the bottom of the transducer. This fluid, or couplant, is needed for transmission of sound between the roll and the transducer. During an automated scan where the roll is being rotated, this couplant layer will leave a trail of water that will interfere with the data taken on the subsequent rotation. U.S. Pat. No. 5,469,743 addresses this issue by proposing a wiper mechanism that eliminates this couplant material as well as water used to cool during grinding. This type apparatus has been found to be unreliable in practice since it cannot eliminate all surface water especially during grinding when water is splashed around the roll.

This patent describes an inspection system that uses an alternative ultrasonic method, Creeping Waves, instead of Surface Waves. Creeping Waves have been found to be highly sensitive to surface breaking cracks but not affected by surface contaminants such as water drops, oil, etc.

Ultrasonic Creeping Waves are produced by propagating high angle Longitudinal Waves into the mill roll at a location underneath the ultrasonic transducer. Since Creeping Waves are nothing more than high angle compression waves, the direction of particle displacements is always in the same direction as the direction of wave propagation. Therefore, no out of plane displacements are produced on the surface of the roll. Therefore, the sound wave is not affected by fluid on the roll surface making inspection possible during grinding processes without the need for water removal mechanisms.

The ideal system for use in the inspection of mill rolls is one that can be operated while the roll is being ground by the grinding machine. During the process of grinding, a large amount of water is sprayed on the roll at the location of the grinding stone. This water is required for cooling of the grinding wheel. This cooling fluid saturates the entire roll. The use of Surface Waves has been found to be impractical while grinding since the roll has to be completely dry in front of the ultrasonic transducer to avoid the possibility of a water drop reflection being interpreted as a surface crack. Surface Waves have been successfully implemented on mill rolls using electromagnetic acoustic transducers. However, this type of ultrasonic transducer does require that the mill roll be completely dried prior to inspection, thus making it impractical for use during the grinding process. This invention is unique since it permits the real-time ultrasonic inspection of a mill roll during the grinding process. With this capability, the operator can monitor the presence of the crack and halt grinding at the moment the crack is no longer detectable. This ability minimizes the amount of roll material removed while maximizing grinder utilization. Performing the roll inspection during grinding also eliminates the time required for roll drying and post grinding inspection.

A system based on the use of Creeping Wave transducers would appear very similar to a system using Surface Waves transducers. Both systems would require transport mechanism that lowers the transducers to the roll surface during testing. Both systems would require a couplant delivery system consisting of tubes providing water to transducer housings. Both systems could be manufactured to inspect for both circumferential defects and axially oriented defects. Two major differences exist between a Surface Wave system and a Creeping Wave system. First, the Creeping Wave system does not require any apparatus for water removal from the roll surface. Secondly, the Creeping Wave system can be used while grinding the roll. Mounting the transducer assembly at the same axial position as the grinding wheel will allow for real-time feed back to the grinder operator on defect removal status. Inspecting for defects during grinding allows the operator to terminate grinding once the defect is no longer detected. This minimizes grinding time and maximizes mill roll life, both a major advantage and cost savings for the mill. Current practice requires that the operator grind the mill roll until a predetermined amount of material has been removed from the roll. The roll is then dried and inspected manually or using an automated system. If a crack is found, the mill roll is ground some more and retested. This process is repeated until the roll is defect free.

SUMMARY OF INVENTION

The mill roll inspection system consists of the ultrasonic transducers, the couplant delivery system and the data acquisition system. The unique component of this system lies in the transducer used and more specifically, the Creeping Wave mode produced by this transducer. The use of this method of ultrasonic inspection permits the inspection of mill rolls while they are wet.

It is an object of the present invention to provide a method to ultrasonically inspect mill rolls using ultrasonic Creeping Waves.

It is another object of this invention to provide an ultrasonic inspection that does not require the drying of the roll surface in front of the transducer assembly prior to performing an inspection.

It is another object of this invention to provide a real-time ultrasonic inspection that can be performed during the grinding operation of a mill roll without the need to remove grinding cooling fluid.

It is still another object of this invention to provide an ultrasonic inspection of mill rolls that is sensitive to surface and near surface defects such as cracks and porosity, without being effected by surface contaminates such as oil or water.

These and other objects will become apparent when reference is had to the drawings.

4.0 BRIEF DESCRIPTION OF DRAWINGS

FIG. 1 is an illustration of a creeping wave propagating along a material surface. This figure shows that the direction of wave induced displacements are parallel to the plane produced by the material surface, resulting in insensitivity to surface contaminates such as water.

FIG. 2 is an illustration of a Surface Wave propagating along a material surface. This figure shows that the direction of wave induces displacements are perpendicular to the plane produced by the material surface, resulting in sensitivity to surface contaminates such as water.

FIG. 3 is a basic layout of a mill roll grinding machine showing the inspection device, grinding wheel and cooling fluid.

FIG. 4 is a cross-sectional view of a creeping wave transducer showing the proper angles of incidence and angle of propagation of the resulting longitudinal wave required to produce creeping waves.

5.0 DESCRIPTION OF INVENTION

Figure 5:
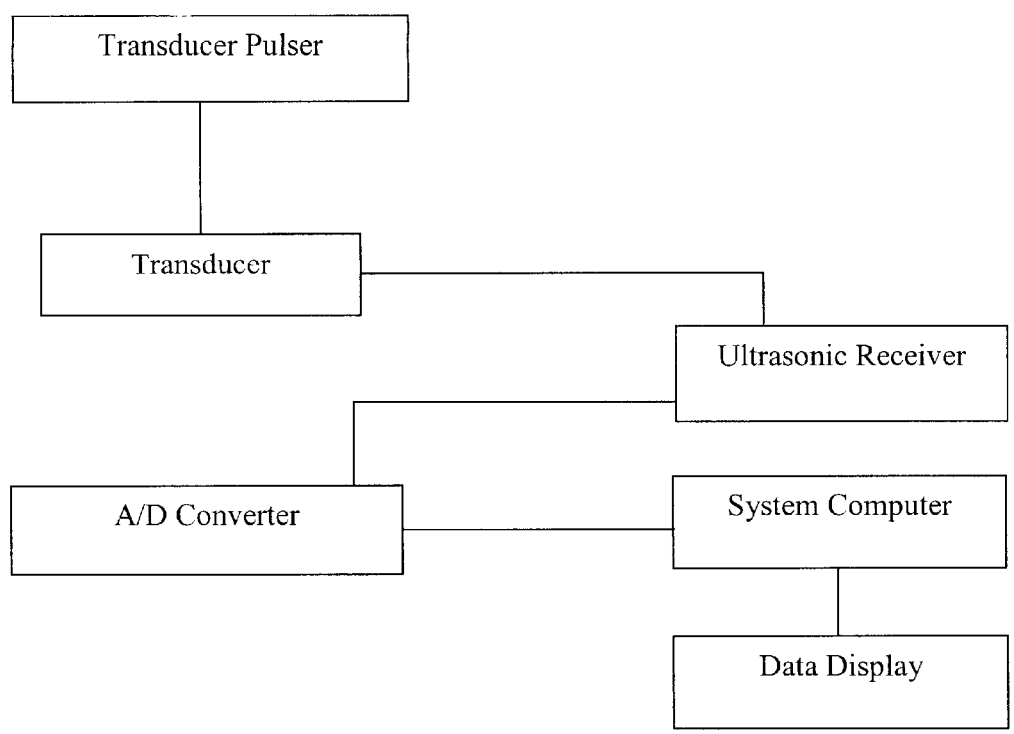
FIG. 5 shows the diagrammatic control system.

The present invention is an ultrasonic inspection system for the detection of surface breaking and near surface defects on mill rolls that uses Creeping Waves, making it possible to inspect a wet roll.

FIG. 3 is an illustration of the mill roll inspection system mounted on a mill roll grinder 19 with stone 18. The inspection system is comprised on four basic components: the transducer assembly 20, the transducer actuator 15, the couplant delivery system 17, and the data acquisition system 21.

The transducer assembly 10 consists of one of more transducers 20 mounted in an articulated holder that allows the bottom surface 12 of each transducer to ride against the surface 13 of the roll 14 over a range of roll diameters. Each transducer can be mounted in any orientation on the mill roll, depending on the orientation of the defect to be detected. Multiple transducers can be used to detect defects of various orientations.

Each transducer 20 is designed to generate a creeping wave, which is defined as a longitudinal wave propagated just beneath the surface of the material. A creeping wave is produced by a transducer that generates a longitudinal wave propagated at or near 80 degrees as shown in FIG. 4. A typical creeping wave transducer designed for use on steel will have an incident angle of approximately 27.5 degrees. Creeping wave transducers also produce a shear wave that propagates at an angle into the material. The shear wave is not used for the inspection of mill rolls. The creeping wave transducers can be of single or dual element design and may require contouring of the bottom surface to fit the contour of the mill roll. Water is provided at outlet 17 which is adjacent to grinding stone 18.

Propagation of a high angle longitudinal wave, such as that described will result in the formation of a Creeping Wave that will follow the contour of the surface. This Creeping wave will travel out in front of the transducer, until it meets a defect. If the defect is oriented so that it is perpendicular to the direction of propagation, a portion of the Creeping wave will be reflected back toward to the transducer where it is detected by the transducer. This type of inspection is referred to as a pulse-echo exam where the presence of a signal indicates the existence of a defect.

The ultrasonic energy is produced by applying a voltage across a piezoelectric crystal which produces small displacement that are transferred from the transducer to the mill roll through a coupling fluid, such as water. Similarly, an ultrasonic wave is detected by entering into the transducer where it vibrates the piezoelectric crystal, whereby producing small electrical signals that are detected by the Data Acquisition System.

Attached to the transducer assembly is the transducer actuator assembly 15. The transducer actuator provides retraction of the transducer assembly to and from the mill roll surface. The ability to remove the transducers from the mill roll is required when testing is not required or when removing the mill roll from the grinder. The actuator 15 can be driven by electric motor, air cylinder or other suitable device.

The couplant delivery system consists of a filter and small tubes 16 used to carry grinder coolant to the transducers. A small pump (not shown) may be necessary to force the liquid through the tubing 16 to the transducers 20. The couplant is applied to the surface of the roll or introduced through special ports machined in the transducer 20 housings. The couplant delivery system must maintain a consistent layer of fluid between the bottom surface of the transducer and the mill roll surface.

The data acquisition system 21 consists for several sub-components including the transducer pulser 22, the ultrasonic receiver 23, the analog/digital converter 24, the system computer 25 and the software used to control the process and display data. The transducer pulser generates high voltage pulses to piezoelectric crystals contained inside each transducer. These electrical pulses are necessary to generate the ultrasonic waves that are used to detect mill roll defects. The ultrasonic receiver 23 takes the low amplitude electrical signals produced by the ultrasonic transducers 20 and provides noise reduction through filtering and amplification. Once the signal has been conditioned by the receiver card, it then passes to the analog-to-digital converter 24 where the analog signal is converted to a digital equivalent. This digital information is then available to the system computer 25, which is programmed to extract information relevant to the presence of a defect. The primary purpose of the system computer is to control the timing, data storage and control of the different hardware components. Also residing on the system computer is the software that provides an interface between the system and the operator. Equally important is the ability of the software to display data as at 26 in such a way that the operator can clearly discern when a defect is present and has been removed. The present invention can be operated during the grinding process allowing the operator to know immediately whether a grinding pass has removed the defect from the mill roll. Data is provided on a system monitor 26 in the form of an image where the surface of the roll is displayed as a defect map with ultrasonic results displayed at the corresponding location that it was collected. The system display is continuously updated as the mill roll is being machined showing test results obtained immediately following the grinding wheel.

What is claimed is:

1. An automated ultrasonic inspection system for roll mills, said system comprising
   - means for rotating a mill roll for simultaneous inspection and grinding means for grinding said mill roll
   - means for introducing a creeping wave propagation to said rotating roll so as to allow for inspection of said roll for cracks and defects, and
   - means to convert said creeping wave propagation system to data useful to an operator of said system whereby the operator can grind said roll in such a way as to rid it of any cracks and defects in its cylindrical surface.

2. A system as in claim 1 wherein said means for introducing a creeping wave propagation is a transducer assembly in contact with the surface of the rotating mill roll.

3. A system as in claim 2 and including a transducer actuator which acts to adjust the transducer so that it can accommodate varying diameter mill rolls.

4. A system as in claim 1 and including means to introduce water to the surface of said rotating mill roll to facilitate the grinding, the means adapted to introduce the water just before the contact of the grinding means with the surface of the mill roll.

5. A system as in claim 2 including means to introduce couplant fluid to the surface of the mill roll where it contacts the transducer assembly.

6. A system as in claim 5 wherein said means to introduce couplant fluid comprises tubing adjacent said transducer assembly.

7. A system as in claim 1 wherein said means to convert said creeping wave propagation to useful data comprises a data acquisition center.

8. A system as in claim 7 wherein said data acquisition center includes a transducer pulser, an ultrasonic receiver to receive impulses from said pulser, an analog to digital converter to convert said pulses and a computer to accept said converted pulses and display them in a data display to the operator.

9. A system as in claim 1 wherein said creeping wave propagation is ultrasonic and has an incident angle of 27.5° and propagates a creeping wave of 80° in a creeping wave zone.

10. A system as in claim 9 wherein said means to produce said creeping wave is a transducer assembly which includes a fluid couplant supply means for supplying couplant fluid to the surface of said rotating mill roll where it is engaged by said transducer assembly.

11. A method of simultaneously inspecting and grinding rotating mill rolls, said method comprising
    - introducing an ultrasonic creeping wave propagation to the surface of said rotating mill roll,
    - converting said propagation to useful data relative to cracks in the surface of said mill roll, and
    - performing both these aforementioned steps while the roll is being ground for the removal of cracks,
    - whereby by performing inspection and grinding simultaneously, real-time information as to the effectiveness of the grinding process is attained.

12. A method as in claim 11 wherein said creeping wave propagation is introduced at about an 80° angle of propagation.

13. A method as in claim 12 and including the step of providing couplant fluid to the surface of said mill roll where the creeping wave propagation is introduced.

14. A method as in claim 12 and including the step of providing water to surface of said mill roll just prior to grinding.

15. A method as in claim 11 which includes the steps of adding couplant fluid and water to the surface of said mill roll.

16. A method as in claim 15 wherein the step of converting the propagation data to data useful to the operator for grinding includes converting the data from analog form to digital form.

\* \* \* \* \*